(12) United States Patent
Sun et al.

(10) Patent No.: US 11,655,208 B2
(45) Date of Patent: May 23, 2023

(54) 1-CARBOXY-2-HYDROXY-3-IMINOPROPANE AND EXTRACTION METHOD THEREOF

(71) Applicant: Jiangnan University, Wuxi (CN)

(72) Inventors: Xiulan Sun, Wuxi (CN); Yongli Ye, Wuxi (CN); Qianqian Hong, Wuxi (CN); Deping Xu, Wuxi (CN); Yinzhi Zhang, Wuxi (CN); Shuxiang Geng, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/548,669

(22) Filed: Dec. 13, 2021

(65) Prior Publication Data

US 2022/0098144 A1 Mar. 31, 2022

(30) Foreign Application Priority Data

Dec. 21, 2020 (CN) .......................... 202011532914.4

(51) Int. Cl.
| | | |
|---|---|---|
| *C07C 249/02* | (2006.01) | |
| *A61K 31/15* | (2006.01) | |
| *B01D 11/02* | (2006.01) | |
| *A61K 36/52* | (2006.01) | |
| *B01D 15/12* | (2006.01) | |
| *B01D 15/42* | (2006.01) | |

(52) U.S. Cl.
CPC ............ *C07C 249/02* (2013.01); *A61K 31/15* (2013.01); *A61K 36/52* (2013.01);
(Continued)

(58) Field of Classification Search
CPC ..... C07C 249/02; C07C 251/08; A61K 31/15; A61K 36/52; B01D 11/0288;
(Continued)

(56) References Cited

U.S. PATENT DOCUMENTS 11,384,109 B2 * 7/2022 Sun .......................... C07H 1/08

FOREIGN PATENT DOCUMENTS

| CN | 110302240 A | 10/2019 |
| CN | 111704639 A | 9/2020 |

OTHER PUBLICATIONS

Translation of Xu et al patent publication CN 10519457A, published Sep. 2009. (Year: 2009).*

(Continued)

*Primary Examiner* — Joseph W Drodge
(74) *Attorney, Agent, or Firm* — IPro, PLLC

(57) ABSTRACT

The present disclosure discloses a 1-carboxy-2-hydroxy-3-iminopropane and an extraction method thereof, and belongs to the technical fields of food, health food and medicine. A method for extracting the 1-carboxy-2-hydroxy-3-iminopropane of the present disclosure includes the following steps: (1) adding a diaphragma juglandis fructus powder into an ethanol solution for extraction and filtration to obtain a supernatant, and conducting concentration on the supernatant under reduced pressure to obtain a walnut alcohol extract; (2) adding a filter residue of step (1) into water for extraction and filtration to obtain a supernatant, and conducting concentration on the supernatant under reduced pressure to obtain a walnut water extract; and (3) mixing the walnut alcohol extract and the water extract to obtain a diaphragma juglandis fructus mixed extract, sequentially conducting elution through an AB-8 type macroporous resin column, an MCI column and an ODS column, and conducting separation to obtain a precipitate, namely the 1-carboxy-2-hydroxy-3-iminopropane. In the present disclosure, the 1-carboxy-2-hydroxy-3-iminopropane in diaphragma juglandis fructus is found for the first time and has great sedation and hypnosis activity.

9 Claims, 3 Drawing Sheets

(52) U.S. Cl.
CPC ...... *B01D 11/0288* (2013.01); *B01D 11/0292* (2013.01); *B01D 15/125* (2013.01); *B01D 15/426* (2013.01)

(58) Field of Classification Search
CPC ... B01D 11/0292; B01D 11/02; B01D 11/028; B01D 15/08; B01D 15/12; B01D 15/125; B01D 15/42; B01D 15/424; B01D 15/426; B01D 37/00; A61P 25/20
See application file for complete search history.

(56) References Cited

OTHER PUBLICATIONS

Translation of Xu et al patent publication CN 107118126, published Jun. 2017. (Year: 2017).*
Qingran et al, "Polysaccharides from Diaphragma juglandis fructus: Extraction optimization, antitumor, and immune-enhancement effects", International Journal of Biological Molecules, vol. 115, pp. 835-845, Published Apr. 27, 2018. (Year: 2018).*
Liu et al, "Identification and Quantification of Bioactive Compounds in Diaphragma juglandis Fructus by UHPLC-MS/MS", Journal of Agricultural and Food Chemistry, vol. 67, pp. 3811-3825, Published Mar. 4, 2019. (Year: 2019).*
Translation of Lobanov et al patent publication RU 270730002, published Nov. 2019. (Year: 2019).*
Translation of Sun et al patent publication CN 1111704639A, published Sep. 2020 (Year: 2020).*
Wilimowski, Marian et. al. "Pharmacologic properties of derivatives of 3-phenyl-3-hydroxyglutaric acid", Archivum Immunologiae et Therapiae Experimentalis 18(2):270-9, Feb. 1970.

* cited by examiner

1-CARBOXY-2-HYDROXY-3-IMINOPROPANE AND EXTRACTION METHOD THEREOF

TECHNICAL FIELD

The present disclosure relates to a 1-carboxy-2-hydroxy-3-iminopropane and an extraction method thereof, and belongs to the technical fields of food, health food and medicine.

BACKGROUND

Diaphragma juglandis fructus is also known as a walnut diaphragm or a walnut valve. In traditional medicinal uses, the diaphragma juglandis fructus is used for treatment and prevention of diabetes, kidney deficiency, diarrhea and diseases of the genitourinary system. In-vivo and in-vitro studies have found that diaphragma juglandis contains flavonoids (3.89%-5.44%), phenols (2.39%-3.54%), saponins (1.86%-5.98%), lignans and other functional ingredients, so that the diaphragma juglandis has many functional activities, such bacteria inhibition, oxidation resistance, tumor prevention and blood sugar and blood lipid reduction. The diaphragma juglandis fructus can be used for development of products in health food, medicine and other related fields.

However, the diaphragma juglandis fructus has complicated components. It is impossible to predict the components in the diaphragma juglandis fructus and effects of the components.

SUMMARY

In order to solve at least one of the problems above, the present disclosure provides a compound 1-carboxy-2-hydroxy-3-iminopropane, which is separated from diaphragma juglandis fructus and has potential activity and effects of sedation and hypnosis. In addition, an extraction method is simple and easy to implement.

A first objective of the present disclosure is to provide a 1-carboxy-2-hydroxy-3-iminopropane, and a structural formula of the 1-carboxy-2-hydroxy-3-iminopropane is shown in Formula I:

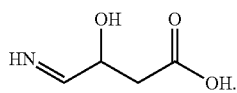

Formula I

A second objective of the present disclosure is to provide a method for extracting the 1-carboxy-2-hydroxy-3-iminopropane from diaphragma juglandis fructus, and the method includes the following steps:

(1) adding a diaphragma juglandis fructus powder into an ethanol solution for extraction and filtration to obtain a supernatant, and conducting concentration on the supernatant under reduced pressure to obtain a walnut alcohol extract;

(2) adding a filter residue obtained by the filtration in step (1) into water for extraction and filtration to obtain a supernatant, and conducting concentration on the supernatant under reduced pressure to obtain a walnut water extract; and (3) mixing the walnut alcohol extract obtained in step (1) and the water extract obtained in step (2) to obtain a diaphragma juglandis fructus mixed extract, sequentially conducting elution on the diaphragma juglandis fructus mixed extract through an AB-8 type macroporous resin column, an MCI column and an ODS column with different concentrations of ethanol, and conducting separation to obtain a precipitate, namely the 1-carboxy-2-hydroxy-3-iminopropane.

In an embodiment of the present disclosure, in step (1), a ratio of the diaphragma juglandis fructus powder to the ethanol solution is 1:8-12 in g/mL, more preferably 1:10.

In an embodiment of the present disclosure, in step (1), the ethanol solution is an ethanol aqueous solution with a concentration of 70-100%, more preferably 70%.

In an embodiment of the present disclosure, in step (1), the extraction is conducted at 55-65° C. for 3-4 hours, and more preferably conducted at 60° C. for 4 hours.

In an embodiment of the present disclosure, in step (1), the diaphragma juglandis fructus powder is obtained by pulverization and sieving with a 40-mesh sieve.

In an embodiment of the present disclosure, in step (1), the extraction process may be repeated, the number of iterations may be 2-4 times.

In an embodiment of the present disclosure, in step (1), the concentration is conducted under reduced pressure until a solid content is 20-30%.

In an embodiment of the present disclosure, in step (2), a mass ratio of the filter residue to the water is 1:(8-12), more preferably 1:10.

In an embodiment of the present disclosure, in step (2), the extraction is conducted at 60° C. for 3-4 hours.

In an embodiment of the present disclosure, in step (2), the extraction process may be repeated, the number of iterations may be 2-4 times.

In an embodiment of the present disclosure, in step (2), the concentration is conducted under reduced pressure until a solid content is 20-30%.

In an embodiment of the present disclosure, in step (3), an ethanol solution used through the AB-8 type macroporous resin column (10 cm×150 cm) includes ethanol aqueous solutions with volume fractions of 0, 30%, 50% and 70%.

In an embodiment of the present disclosure, in step (3), an ethanol solution used through the MCI column includes ethanol aqueous solutions with volume fractions of 0, 10%, 30% and 50%.

In an embodiment of the present disclosure, in step (3), an ethanol solution used through the ODS column includes ethanol aqueous solutions with volume fractions of 0, 5%, 10% and 20%.

In an embodiment of the present disclosure, in step (3), after the elution is completed each time, an eluted fraction is collected, concentrated under reduced pressure until a solid content is 15-20% and then loaded.

In an embodiment of the present disclosure, in step (3), the elution may be repeated, the number of iterations may be 3-10 times through the column.

A third objective of the present disclosure is to provide application of the 1-carboxy-2-hydroxy-3-iminopropane in the field of medicine.

In an embodiment of the present disclosure, the application includes using the 1-carboxy-2-hydroxy-3-iminopropane to achieve the effects of sedation and hypnosis.

A fourth objective of the present disclosure is to provide a medicinal preparation, which includes the 1-carboxy-2-hydroxy-3-iminopropane as an ingredient.

The present disclosure has the following beneficial effects:

(1) In the present disclosure, a new compound 1-carboxy-2-hydroxy-3-iminopropane in the diaphragma juglandis fructus is found for the first time, and pharmacological tests have proved that the compound has great sedation and hypnosis activity.

(2) By using the 1-carboxy-2-hydroxy-3-iminopropane of the present disclosure, a sleep latency period is shortened by 24.62% ($P<0.05$), and a sleep duration period is prolonged by 61.49% ($P<0.05$).

DETAILED DESCRIPTION

Preferred embodiments of the present disclosure are described below. It should be understood that the embodiments are used to better explain the present disclosure, rather than limit the present disclosure.

Example 1

A method for extracting 1-carboxy-2-hydroxy-3-iminopropane from diaphragma juglandis fructus included the following steps:

(1) 10 kg of the diaphragma juglandis fructus was weighed, pulverized and sieved with a 40-mesh sieve, an ethanol solution with a volume fraction of 70% was added according to a material liquid mass-volume ratio of 1:10 (kg/L), stirring extraction was conducted at 60° C. for 4 hours, and filtration was conducted to obtain a filtrate; a filtrate residue was subjected to alcohol extraction again by using the method above to obtain a filtrate; and the two filtrates were combined, concentration was conducted under reduced pressure until a solid content was 30% to obtain a diaphragma juglandis fructus ethanol extract, and then the diaphragma juglandis fructus ethanol extract was frozen and stored at −20° C.;

(2) a filter residue obtained after the alcohol extraction of the diaphragma juglandis fructus was added into water according to a material liquid mass-volume ratio of 1:10 (kg/L), stirring extraction was conducted at 60° C. for 4 hours, and filtration was conducted to obtain a filtrate; a filtrate residue was subjected to water extraction again by using the method above to obtain a filtrate; and the two filtrates were combined, and then concentration was conducted under reduced pressure until a solid content was 30% to obtain a diaphragma juglandis fructus water extract; and (3) the walnut alcohol extract obtained in step (1) and the water extract obtained in step (2) were mixed to obtain a diaphragma juglandis fructus mixed extract; 1,000 g of the diaphragma juglandis fructus mixed extract was sequentially subjected to gradient elution through an AB-8 type macropores resin column (10 cm×150 cm) with water, 30% ethanol, 50% ethanol and 70% ethanol, and a water eluted fraction was collected, concentrated under reduced pressure until a solid content was 20% and then loaded onto an MCI column; the water eluted fraction was sequentially subjected to gradient elution with water, 10% ethanol, 30% ethanol and 50% ethanol, and a water eluted fraction was collected, concentrated under reduced pressure until a solid content was 20% and then loaded onto an ODS column; and the water eluted fraction was sequentially subjected to gradient elution with water, 5% ethanol, 10% ethanol and 20% ethanol, fractions were collected and repeatedly purified and eluted, and then separation was conducted to obtain a precipitate, namely, the 1-carboxy-2-hydroxy-3-iminopropane.

The precipitate (white amorphous powder) obtained was tested, and test results were as follows.

Figure 1:
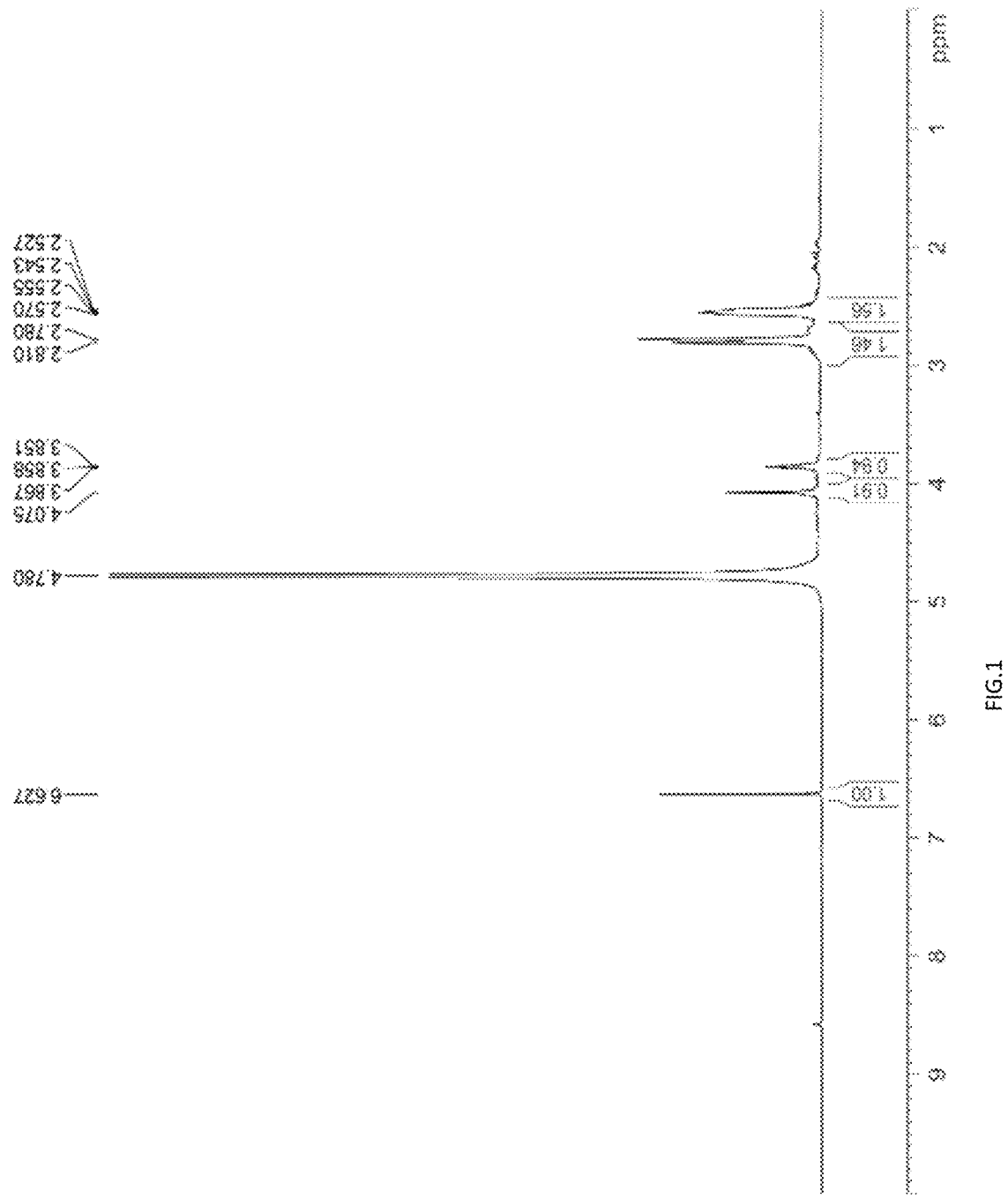
FIG. 1 is a [1]hydrogen-nuclear magnetic resonance ($^1$H-NMR) spectrum of a compound obtained in Example 1.

FIG. 1 was a $^1$H-NMR spectrum of the compound obtained in Example 1. From FIG. 1, it could be seen that in the spectrum, there were 5 hydrogen signals including $\delta_H$ 6.63 (1H, s), 4.07 (1H, s), 3.86 (1H, s, J=4 HZ), 2.79 (1H, d, J=15 HZ) and 2.63 (1H, dd, J=7.5, 8 HZ), where $\delta_H$ 4.07 was the hydrogen signal of oxygen-linked carbon, and 2.79 and 2.63 were the hydrogen signal of —$CH_2$—.

Figure 2:
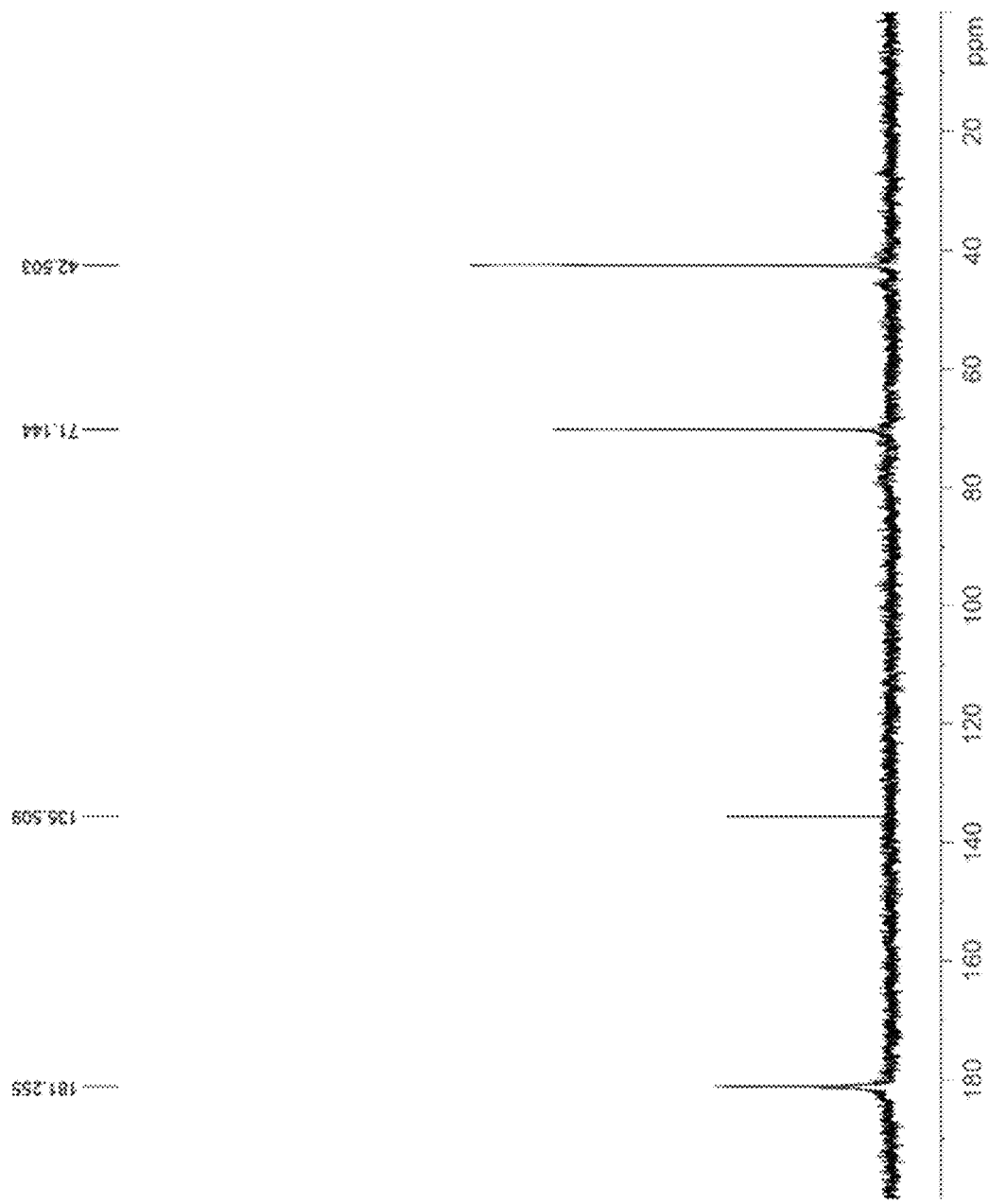
FIG. 2 is a [13]carbon-NMR ($^{13}$C-NMR) spectrum of the compound obtained in Example 1.

FIG. 2 was a $^{13}$C-NMR spectrum of the compound obtained in Example 1. From FIG. 2, it could be seen that in the spectrum, there were 4 carbon signals including δ181.2 (—COOH), 135.5, 70.2 and 42.5.

Figure 3:
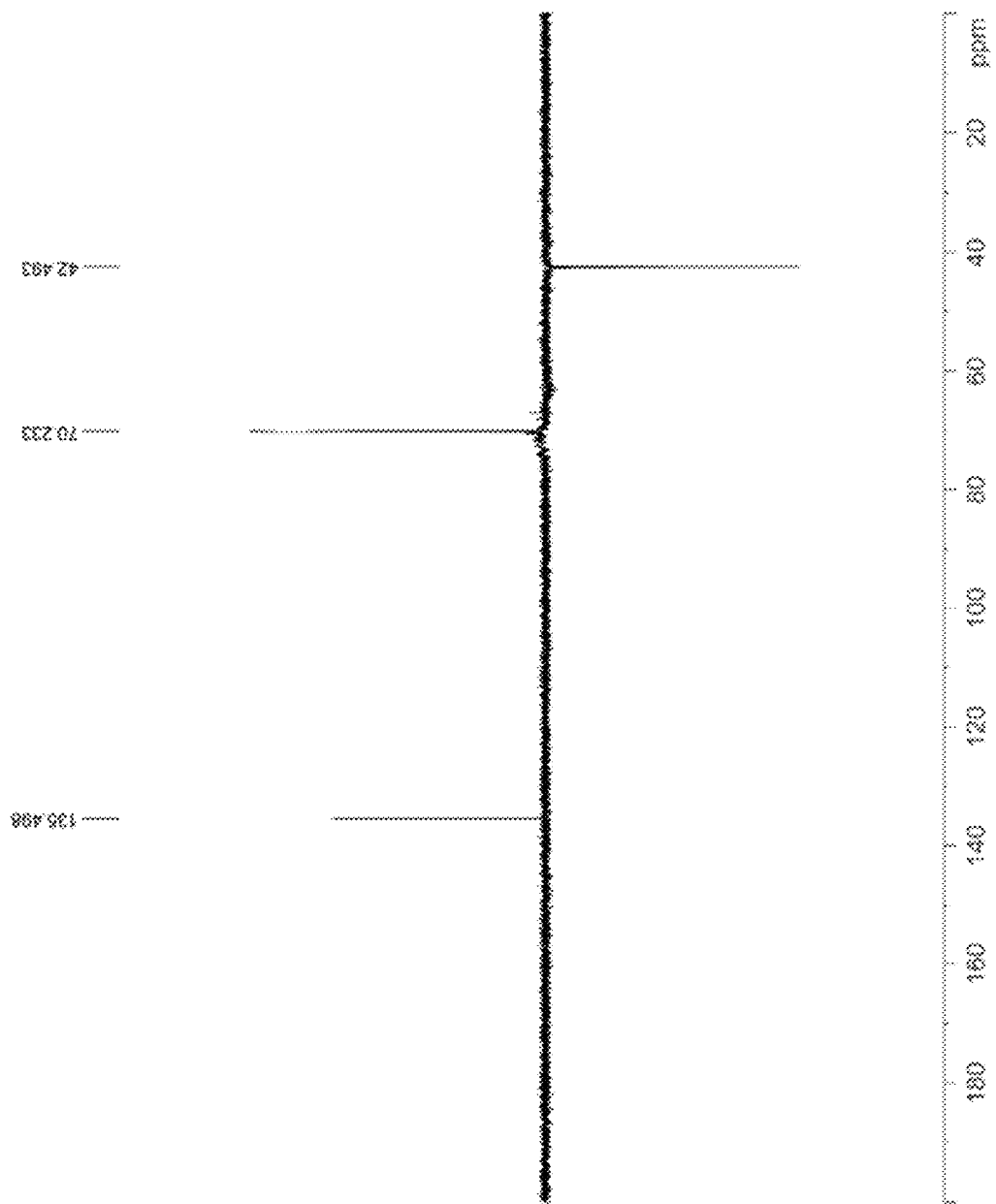
FIG. 3 is a [135]distortionless enhancement by polarization transfer-NMR ([135]DEPT-NMR) spectrum of the compound obtained in Example 1.

FIG. 3 was a [135]DEPT-NMR spectrum of the compound obtained in Example 1. From FIG. 3, it could be seen that 6135.5 was the carbon signal of —CH—. According to chemical shift, it was inferred that the —CH— was connected to an imino group by a double bond, 670.2 was an oxygen-linked carbon signal, and 642.5 was the carbon signal of the —$CH_2$—.

According to FIG. 1 to FIG. 3, it was proved that the compound 1-carboxy-2-hydroxy-3-iminopropane was obtained by extraction in Example 1.

Example 2 Application of 1-carboxy-2-hydroxy-3-iminopropane

The sedation and hypnosis activity of the 1-carboxy-2-hydroxy-3-iminopropane obtained in Example 1 was tested, and specific operation was as follows:

30 SPF-level 4-week-old male ICR (Institute of Cancer Research) mice were adaptively reared for 1 week and then randomly divided into 3 groups with 10 mice in each group. An experimental group and a blank group were given an aqueous solution of the 1-carboxy-2-hydroxy-3-iminopropane and water at a dose of 1.0 g/kg·bw by gavage respectively, and a positive control group was given an aqueous solution of estazolam at a dose of 2 mg/kg·bw by the gavage. After continuous gavage for 14 days, tests were carried out. The tests were carried out around 25° C. in a quiet environment.

The mice were subjected to behavioral tests, and experimental processes were as follows.

1. Open Field Test

An open field maze of 4 units (each unit 50 cm×50 cm×38 cm) consisting of 4 activity spaces were used in the test, and 4 mice were tested each time. The open field spaces were cleaned with alcohol before the test, and the test was started 30 minutes after a sample group was administered (15 minutes after a positive control group was administered). During the test, tails of the mice were gently grasped, and the mice were placed in the middle of each unit of the open field maze for adaption for 5 minutes. A software start button was clicked to activate software for tracking moving paths of the mice. With an average movement speed, a movement time and a stay time in the middle area within 10 minutes as indexes, data analysis was conducted by using EthoVision XT 11 software. After each test was completed, urine and feces were cleaned, and a bottom and an inner wall of the maze were sprayed with 5-10% ethanol and then wiped with paper to remove an odor left by the mice. Then, a next group of the mice was tested, and influence of the odor and residue on the next group of the mice was avoided.

2. Direct Sleep Observation Test

After the open field test was completed, a direct sleep observation test was carried out the next night. 30 minutes after the gavage, a surveillance camera was used for observation, and a sleep time of the mice in each group within 12 hours after the gavage was recorded.

3. Pentobarbital Sodium Induced Sleep Test

Before the test, a preliminary test was carried out to determine a dose of pentobarbital sodium by intraperitoneal injection. After the intraperitoneal injection, the dose when all mice fell asleep for a moderate time was used as a standard, and the test was carried out with this dose (50 mg/kg·bw). 30 minutes after the last gavage, the mice were given the pentobarbital sodium by intraperitoneal injection to induce sleep. The time from injection of the pentobarbital sodium to disappearance of a righting reflex was recorded as a sleep latency period of the mice. The time from the disappearance of the righting reflex to reappearance of the righting reflex was recorded as a sleep latency period of the mice. Whether or not the latency period of each group was shortened and whether or not the sleep time was prolonged were observed.

Test results were as follows.

Table 1 showed test results of the movement speed, movement time and stay time in the middle area of the mice in the blank group, the experimental group and the positive control group. From Table 1, it could be seen that the 1-carboxy-2-hydroxy-3-iminopropane significantly reduced the movement speed and the movement time of the mice (P<0.05) were, and significantly increased the stay time in the middle area of the mice (P<0.01).

TABLE 1

Test results of the movement speed, movement time and stay time in the middle area of the mice in the blank group, the experimental group and the positive control group (x ± s)

| Group | Movement speed (cm · s$^{-1}$) | Movement time (s) | Stay time in the middle area (%) |
|---|---|---|---|
| Blank group | 6.22 ± 1.27 | 421.20 ± 63.41 | 9.80 ± 2.34 |
| Experimental group | 4.66 ± 1.14* | 333.76 ± 56.84** | 17.81 ± 5.14** |
| Positive control group | 4.60 ± 0.96* | 325.85 ± 51.64** | 20.63 ± 9.01** |

Note:
*represented P < 0.05,
**represented P < 0.01, and the two groups were compared with the blank group.

Table 2 showed test results of a natural 12 h sleep duration period, a pentobarbital sodium induced sleep latency period and a pentobarbital sodium induced sleep time of the mice in the blank group, the experimental group and the positive control group (x±s). From Table 2, it could be seen that by using the 1-carboxy-2-hydroxy-3-iminopropane, a total sleep duration period within 12 hours was longer than that of the blank group, and there was a statistical difference (P<0.05). According to the results of the pentobarbital sodium induced sleep test, it was shown that by using the 1-carboxy-2-hydroxy-3-iminopropane, the sleep latency period was shortened by 24.62% (P<0.05), and the sleep duration period was prolonged by 61.49% (P<0.05). It was indicated that the 1-carboxy-2-hydroxy-3-iminopropane had significant sedation and hypnosis activity.

TABLE 2

Test results of the natural 12 h sleep duration period, the pentobarbital sodium induced sleep latency period and the pentobarbital sodium induced sleep time of the mice in the blank group, the experimental group and the positive control group (x ± s)

| Group | 12 h sleep duration period (min) | Latency period (s) | Sleep duration period (%) |
|---|---|---|---|
| Blank group | 289.89 ± 31.54 | 4.54 ± 0.75 | 17.92 ± 4.57 |
| Experimental group | 374.33 ± 24.48** | 3.60 ± 0.368** | 34.73 ± 12.71** |
| Positive control group | 404.10 ± 34.03** | 2.81 ± 0.57** | 66.37 ± 21.05** |

Note:
*represented P < 0.05,
**represented P < 0.01, and the two groups were compared with the blank control group.

What is claimed is:

1. A composition comprising 1-carboxy-2-hydroxy-3-iminopropane, having a structural formula of the 1-carboxy-2-hydroxy-3-iminopropane as shown in Formula I of:

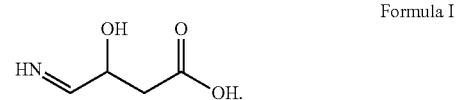

Formula I

2. A method for extracting the 1-carboxy-2-hydroxy-3-iminopropane of claim 1 from diaphragma juglandis fructus, comprising the following steps:
   (a) adding a diaphragma juglandis fructus powder into an ethanol solution for extraction and filtration to obtain a supernatant, and conducting concentration of the supernatant under reduced pressure to obtain a walnut alcohol extract;
   (b) adding a filter residue obtained by the filtration in step (a) into water for extraction and filtration to obtain a supernatant, and conducting concentration of the supernatant under reduced pressure to obtain a walnut water extract; and
   (c) mixing the walnut alcohol extract obtained in step (a) and the walnut water extract obtained in step (b) to obtain a diaphragma juglandis fructus mixed extract, sequentially conducting elution on the diaphragma juglandis fructus mixed extract through an AB-8 type macroporous resin column, an MCI column, and an ODS column with aqueous solutions having different concentrations of ethanol, and conducting separation of the mixed extract to obtain a precipitate, of the 1-carboxy-2-hydroxy-3-iminopropane.

3. The method according to claim 2, wherein in step (a), a ratio of the diaphragma juglandis fructus powder to the ethanol solution is 1:8 g/mL to 1:12 g/mL.

4. The method according to claim 2, wherein in step (a) and step (b), the extraction is conducted at 55° C. to 65° C. for 3 to 4 hours.

5. The method according to claim 2, wherein in step (a) and step (b), the concentration of the walnut alcohol extract and the concentration of the walnut water extract are conducted under reduced pressure until a solid content of the mixed extract is 20% to 30%.

6. The method according to claim 2, wherein in step (c), aqueous solutions are passed through the AB-8 type macroporous resin column comprising aqueous solutions with volume fractions of 0%, 30%, 50%, and 70% ethanol.

7. The method according to claim 2, wherein in step (c), aqueous solutions are passed through the MCI column comprising aqueous solutions with volume fractions of 0%, 10%, 30%, and 50% ethanol.

8. The method according to claim 2, wherein in step (c), aqueous solutions are passed through the ODS column comprises ethanol aqueous solutions with volume fractions of 0%, 5%, 10%, and 20% ethanol.

9. A medicinal preparation, comprising the 1-carboxy-2-hydroxy-3-iminopropane as defined in claim 1.

\* \* \* \* \*